(12) United States Patent
Tsaur (10) Patent No.: US 7,807,612 B2
(45) Date of Patent: Oct. 5, 2010

(54) FATTY ACYL ISETHIONATE PRODUCT-CONTAINING LIQUID CLEANSING COMPOSITIONS STABILIZED WITH MIXTURE OF LONG CHAIN AND SHORT CHAIN FATTY ACIDS/FATTY SOAPS

(75) Inventor: Liang Sheng Tsaur, Norwood, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 11/958,471

(22) Filed: Dec. 18, 2007

(65) Prior Publication Data

US 2009/0156450 A1 Jun. 18, 2009

(51) Int. Cl.
*A61K 7/00* (2006.01)
(52) U.S. Cl. ............... 510/130; 510/136; 510/156; 510/424; 510/481; 510/492
(58) Field of Classification Search .......... None
See application file for complete search history.

(56) References Cited

U.S. PATENT DOCUMENTS

| | | | |
|---|---|---|---|
| 3,723,325 A | 3/1973 | Parran, Jr. | |
| 4,565,647 A | 1/1986 | Llenado | |
| 5,009,814 A | 4/1991 | Kelkenberg et al. | |
| 5,132,037 A | 7/1992 | Greene et al. | |
| 5,234,619 A * | 8/1993 | Greene et al. | 510/131 |
| 5,290,471 A | 3/1994 | Greene et al. | |
| 5,372,751 A | 12/1994 | Rys-Cicciari et al. | |
| 5,389,279 A | 2/1995 | Au et al. | |
| 5,415,810 A | 5/1995 | Lee et al. | |
| 5,739,365 A | 4/1998 | Brody et al. | |
| 5,952,286 A | 9/1999 | Puvvada | |
| 6,077,816 A | 6/2000 | Puvvada | |

| | | | |
|---|---|---|---|
| 2004/0224863 A1 | 11/2004 | Sun et al. | |
| 2005/0136026 A1 | 6/2005 | Qiu | |

FOREIGN PATENT DOCUMENTS

| | | |
|---|---|---|
| EP | 1 479 365 | 11/2004 |
| JP | 63 243200 | 10/1988 |
| JP | 002474464 | 10/1988 |
| WO | 97/05857 | 2/1997 |

(Continued)

OTHER PUBLICATIONS

International Search Report on Application No. PCT/EP2008/060835 dated Jan. 26, 2009 (equivalent to related U.S.Appl. No. 11/850,159).

(Continued)

*Primary Examiner*—Necholus Ogden, Jr.
(74) *Attorney, Agent, or Firm*—Ronald A. Koatz (57) ABSTRACT

The invention provides personal care or hair liquid cleansing compositions comprising fatty acyl isethionate products having more than 5% by wt. free fatty acid/fatty soaps which are stabilized using specific mixture of long chain and short chain fatty acids/fatty soaps; as well as by using proper ratio of total linear fatty acid/fatty soap to total synthetic surfactants (the total synthetic is the sum of (1) fatty acyl surfactant component of (a)—that is, the "pure" fatty acyl isethionate which does not include free fatty acids and/or fatty acid soaps in the fatty acyl surfactant "product"—and (2) the synthetic co-surfactant of (b)).

6 Claims, 1 Drawing Sheet

FOREIGN PATENT DOCUMENTS

| WO | 99/32069 | 7/1999 |
|---|---|---|
| WO | 00/21492 | 4/2000 |
| WO | 03/017968 | 6/2003 |
| WO | 2008/074617 A | 6/2008 |

OTHER PUBLICATIONS

International Preliminary Examination Report on Application No. PCT/EP2007/063128 (equivalent to related U.S. Appl. No. 11/613,617).

Co-pending application for: Applicant: Tsaur et al.; U.S. Appl. No. 12/235,955, filed Sep. 23, 2008, entitled Stable Cleansing Compositions Containing Fatty Acyl Isethionate Surfactant Products Having More Than 10 wt. % of Fatty Acid/Fatty Soap Content Using High Level of Polyol and Methods Thereof.

International Search Report on Application No. PCT/EP2008/067530 dated Jul. 24, 2009.

PCT Search Report on International Application No. PCT/EP2007/063128 dated Apr. 15, 2008.

Co-pending case for Tsaur, filed Dec. 20, 2006; U.S. Appl. No. 11/613,617; U.S. Publication No. 2008/0153729.

Co-pending case for Tsaur, filed Dec. 20, 2006; U.S. Appl. No. 11/613,696; U.S. Publication No. 2008/0153730.

Co-pending case for Tsaur, filed Dec. 20, 2006; U.S. Appl. No. 11/613,617; U.S. Publication No. 2008/0153727.

Co-pending case for Tsaur, filed Sep. 5, 2007; U.S. Appl. No. 11/850,159.

\* cited by examiner

FIG. 1
VISCOSITY PROFILE OF COMPARATIVE EXAMPLE 1A

FIG. 2
DSC TRACE OF COMPARATIVE EXAMPLE 1A

FATTY ACYL ISETHIONATE PRODUCT-CONTAINING LIQUID CLEANSING COMPOSITIONS STABILIZED WITH MIXTURE OF LONG CHAIN AND SHORT CHAIN FATTY ACIDS/FATTY SOAPS

FIELD OF THE INVENTION

The invention is directed to personal care skin or hair liquid cleansing compositions. In particular, it relates to such personal care skin or hair cleansing compositions in which fatty acyl isethionate surfactants products having more than 5 wt % of free fatty acid/fatty soaps are used in the liquid composition. The liquid compositions in which the surfactants are found are stabilized with a specific mixture of long chain and short chain fatty acids/fatty soaps, wherein linear long chain fatty acids/fatty soaps (>14 carbons) comprise more than 20 wt % and less than 70 wt % of total fatty acids/fatty soaps in said liquid compositions.

BACKGROUND OF THE INVENTION

Fatty acyl isethionates (e.g., cocoyl isethionates) are anionic surfactants highly desirable in personal care skin or hair cleansing products, particularly in personal care products, because they lather well, are mild to the skin and have good emollient properties. Typically, fatty acid isethionates are produced by esterification of fatty acids or by reaction of fatty acid chloride having carbon chain length of $C_8$ to $C_{20}$ with isethionate. A typical fatty acyl isethionate surfactant product (e.g., commercially sold or made surfactant product) contains about 40 to 95 wt. % fatty acyl isethionate, and 0 to 50 wt. %, typically 5 to 40 wt. % free fatty acid, in addition to isethionate salts, typically at less than 5%, and trace (less than 2 wt. %) of other impurities A problem with the ready use of commercially sold or made fatty acyl isethionate product in liquid compositions, especially wherein the acyl isethionate surfactant product is used as a primary surfactant, is the low solubility of these compounds in water. This is especially true for fatty acyl isethionate surfactant product containing high level of free fatty acid/fatty soaps (10% by wt. or higher) and/or long chain fatty acyl isethionates component with carbon chain length 14 and higher. The fatty acyl isethionate component of the surfactant product tends to form insoluble surfactant crystals with the amount of crystals depending strongly on the storage temperature due to the wide range of dissolution temperatures of these crystals. This in turn results in unstable liquid cleansers which exhibit very thick or very thin consistency at low and elevated temperatures. At low temperature, the liquid composition becomes a semi-solid gel which is difficult to use. At elevated temperature, the liquid composition turns into water-thin liquid which causes phase separation of the product. This is exemplified in FIG. 1 in which the viscosity at 25 and 40° C. of Comparative Example 1A is shown. Comparative Example 1A is a liquid which contains 36 wt % of fatty acyl isethionate product (Dove® Noodle) and has a viscosity ratio at 40° C., to 25° C., of about 0.0234 when measured at 0.01 s$^{-1}$. At 25° C., this liquid has very high viscosity; and the liquid composition becomes water thin at 40° C.

It would therefore be of tremendous advantage to have compositions, particularly those where fatty acyl isethionate surfactant product with 10 wt % of more free fatty acids is used, having consistent viscosity at both low and elevated temperatures. It would further be advantageous to have a way of manipulating compositional ingredients to ensure such consistent viscosity is obtained and that fatty acyl isethionate product, no matter what their free fatty acid/fatty soap content or what the chain lengths of the fatty acyl isethionate, fatty acid or fatty acid/fatty soap component, can be readily used in a liquid cleanser composition. The present invention provides precisely such compositions and processes for making such compositions.

While not wishing to be bound by theory, applicants believe the problem of inconsistent viscosity and physical instability at elevated temperatures (i.e. 40° C. or higher) for these liquid compositions is caused because the compositions contain insoluble fatty acid/fatty acyl isethionate surfactant crystals at room temperature. Applicants believe the noted stability problems can be resolved by forming viscous surfactant liquid crystals at a temperature at or above the dissolution temperature of these fatty acid/fatty acyl isethionate crystals such that the liquid composition in which the surfactant product will be used has a high enough viscosity to ensure stability, said stability being defined by the absence of visible physical separation after two weeks of storage at 45° C. Formation of such viscous crystals in turn is accomplished by using specific mixture of long chain (>14) and short chain ($\leq C14$) linear fatty acids/fatty soaps (i.e., >20, but less than 70 wt. % of total fatty acids/fatty soaps is long chain fatty acids) in the liquid compositions to create a higher viscosity at elevated storage temperatures (more consistent viscosity) which allows fatty acyl isethionate product, regardless of free fatty acid content or the chain length of isethionates, to have more consistent viscosity at low and elevated temperatures and to be storage stable.

Acyl isethionate liquids do exist in the art. U.S. Pat. No. 5,415,810 to Lee et al., for example, discloses compositions comprising fatty acyl isethionates and zwitterionic surfactant (e.g., cocoamidopropyl betaines), presumably to help solubilize the isethionate and make an isotropic liquid. The reference separately teaches away use of free fatty acids, especially longer chain fatty acids (column 2, lines 34-39), let alone the use of both long chain and short chain fatty acids in combination.

U.S. Pat. No. 5,739,365 to Brody et al. and U.S. Publication No. 2004/0224863 both disclose use of synthetic surfactants having ammonium counterion to help solubilize fatty acid isethionate.

U.S. Pat. No. 5,952,286 and U.S. Pat. No. 6,077,816, both to Puvvada, disclose liquid cleansing compositions which may contain acyl isethionates and which comprise soluble, lamellar phase inducing structurant (e.g., branched fatty acid).

U.S. Pat. No. 5,132,037 to Greene et al. (and related U.S. Pat. No. 5,234,619 and U.S. Pat. No. 5,290,471) disclose compositions with $C_8$ to $C_{22}$ acyl isethionates, synthetics, and free fatty acids, preferably $C_{16}$ or higher. Free fatty acids of 8-22 carbons are incorporated within the compositions claimed in these patents to operate as lather enhancing agents and as skin feel, lubricity, and creaminess enhancers rather than as stabilizer to maintain liquid consistency at low and high temperature storage conditions (lines 29 to 39, column 2 of U.S. Pat. No. 5,132,037). There is no teaching on how to use a specific mixture and the required level of long chain and short chain fatty acids to provide consistent viscosity of liquid composition containing fatty acyl isethionate surfactant products. These patents broadly claimed fatty acid composition (C8 to C22) and its level (1/10 to 10/1 of fatty acids to fatty acyl isethionate surfactants) and are silent to the problem of product inconsistency and storage stability at high temperature for liquid compositions containing insoluble fatty acids/fatty acyl isethionate surfactant crystals. All the comparative examples of the subject invention with compositions as claimed in these patents (Table 3 below) show these liquids of Greene et al. are not stable at 45° C. These comparative examples all showed phase separation in less than 2 weeks at 45° C. storage condition. Compositions that can provide consistent viscosity at elevated temperature stability are not obvious or predictable based on a broad disclosure of fatty acid and fatty acid/surfactant ratio in these patents. It would not be a function of product optimization either since the previous art would not have been aware of what caused the problem and it is completely unpredictable that this is an approach that could work.

Applicants filed in December 2006 three cases relating to liquid compositions with crystal modifier systems similar to those of the subject invention. It would not have been predictable in any of these applications, however, that the specific level of long chain and short chain fatty acids/fatty soaps mixture alone could be used to stabilize liquid compositions containing fatty acyl isethionate surfactant product, e.g., by forming viscous surfactant liquid crystals upon the dissolution of fatty acyl isethionate/fatty acid crystals at elevated temperatures (40° C. or above).

None of the references, alone or together, teach or suggest compositions comprising fatty acyl isethionate surfactant containing specific long chain and short fatty acid/fatty soaps mixture (20 to 70%>C14 and 80 to 30%≦C14) where and the compositions formed have a product viscosity less sensitive to temperature, and are stable at elevated temperature storage conditions.

BRIEF SUMMARY OF THE INVENTION

In one embodiment, the present invention relates to novel liquid cleansing compositions containing fatty acyl isethionate surfactant product which compositions are stabilized with a specific combination of long chain and short chain fatty acids/fatty soaps to increase the viscosity of the liquid composition at elevated temperatures.

More specifically, the invention comprises liquid cleansing compositions comprising:
(a) 3 to 45 wt %, preferably 8 to 35% by wt. of fatty acyl isethionate surfactant product wherein said product comprises fatty acyl isethionate as well as free fatty acids and/or fatty soaps in said product;
(b) 0 to 15% wt % of a co-surfactant selected from the group consisting of anionic (excluding the fatty acyl isethionate component of the fatty acyl isethionate product of (a)), amphoteric and nonionic surfactants and mixture thereof;
(c) 4 to 20 wt % C8 to C20 total linear fatty acids/fatty soaps, which total includes the sum of both the free fatty acids/fatty soaps which are part of the fatty acyl isethionate surfactant product of item (a) as well as linear fatty acid found independently in the composition; in which fatty acids/fatty soaps with carbon chain length longer than 14 comprise 20 to 70 wt %, preferably 30 to 65 wt %, more preferably 30 to 60% by wt. of said total linear fatty acids/fatty soaps in the composition (it is noted that by linear is meant straight-chain, saturated fatty acid);
Ratio of total linear fatty acid/fatty soap to total synthetic surfactants (defined as the sum of fatty acyl isethionate surfactant of item (a), not including the free fatty acids and or fatty acid soaps in the product, and synthetic co-surfactant of item (b)) is at least 0.25, preferably at least 0.30 and less than 1.0.
wherein viscosity of the said liquid cleanser composition at 0.01 s$^{-1}$ should be at least 50 Pas, preferably at least 100 Pas at 25° C.; and the ratio of the viscosity at 40° C. to the viscosity at 25° C., when measured at 0.01 s$^{-1}$, should be at least 0.2, preferably 0.3, most preferably 0.4; the pH of the liquid composition is in the range of 4.0 to 8.0, preferably 4.5 to 7.5; the said composition is stable (i.e., is physically stable and will not partition as can be visually observed) at 45° C. for at least 2 weeks.

In a second embodiment, the invention relates to a process for making such compositions using fatty acyl isethionate surfactant product, co-surfactant, and elevated temperature storage stabilizing system as noted above.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—relevant part—incorporated herein by reference.

DETAILED DESCRIPTION OF THE INVENTION

The present invention relates to novel liquid cleansing compositions containing fatty acyl isethionate surfactant product which are stabilized with a specific combination of long chain and short chain fatty acids (>20 to <70% of all linear fatty acid must be >C14). The fatty acids are used to increase the viscosity of the liquid composition at elevated temperatures.

More specifically, the invention comprises liquid cleansing compositions comprising:
(a) 3 to 45 wt %, preferably 4 to 40% of fatty acyl isethionate surfactant product containing free fatty acids and/or fatty soaps in the said product;

(b) 0 to 15% wt % of a co-surfactant selected from the group consisting of anionic (excluding fatty acyl isethionate of (a)), amphoteric and nonionic surfactants and mixture thereof;

(c) 4 to 20 wt % C8 to C20 linear fatty acids/fatty soaps including the free fatty acids/fatty soaps in the fatty acyl isethionate surfactant product of item (a), in which linear fatty acids/fatty soaps with carbon chain length longer than 14 is 20 to 70 wt %, preferably 30 to 65 wt %, more preferably 30 to 60% by wt. of total linear fatty acids/fatty soaps in the composition;

Ratio of total linear fatty acid/soap to total synthetic surfactants (pure fatty acyl isethionate surfactant of item (a) and synthetic co-surfactant of item (b)) is at least 0.25, preferable 0.30 and less than 1.0.

wherein viscosity of the said liquid cleanser composition at 0.01 s$^{-1}$ should be at least 50 Pas, preferably at least 100 Pas at 25° C.; and the ratio of the viscosity at 40° C. to the viscosity at 25° C., when measured at 0.01 s$^{-1}$, should be at least 0.2, preferably 0.3, most preferably 0.4; the pH of the liquid composition is in the range of 4.0 to 8.0, preferably 4.5 to 7.5; wherein said composition is stable (i.e., is physically stable and will not partition as can be visually observed) at 45° C. for at least 2 weeks.

In a second embodiment, the invention relates to a process for making such compositions using fatty acyl isethionate surfactant product, co-surfactant, and combination of elevated temperature storage stabilizing system as noted above.

The invention is defined in greater detail below.

DEFINITIONS

For purposes of this invention, a fatty acyl isethionate "product" comprises (in addition to other components) both pure fatty acyl isethionates surfactant as well as free fatty acid and/or fatty acid salt.

Fatty Acyl Isethionate Surfactant Product

Compositions of the invention comprise 3 to 45% by wt. fatty acyl isethionate surfactant product with more than 5 wt %, preferably more than 10 wt % of free fatty acid/fatty soap in the surfactant product.

Fatty acyl isethionate surfactant are typically prepared by the reaction of an isethionates salt such as alkali metal isethionates and an aliphatic fatty acid having 8 to 20 carbon atoms and Iodine Value (measuring degree of unsaturation) of less than 20 g, for example:

HOR$^1$SO$_3$M+RCOOH→RCOOR$^1$SO$_3$H where R$^1$ is an aliphatic hydrocarbon radical containing 2 to 4 carbons;

M is alkali metal cation or metal ion (e.g., sodium, magnesium, potassium, lithium), ammonium or substituted ammonium cation or other counterion; and R is an aliphatic hydrocarbon radical having 7 to 24, preferably 8 to 22 carbons.

Figure 1:
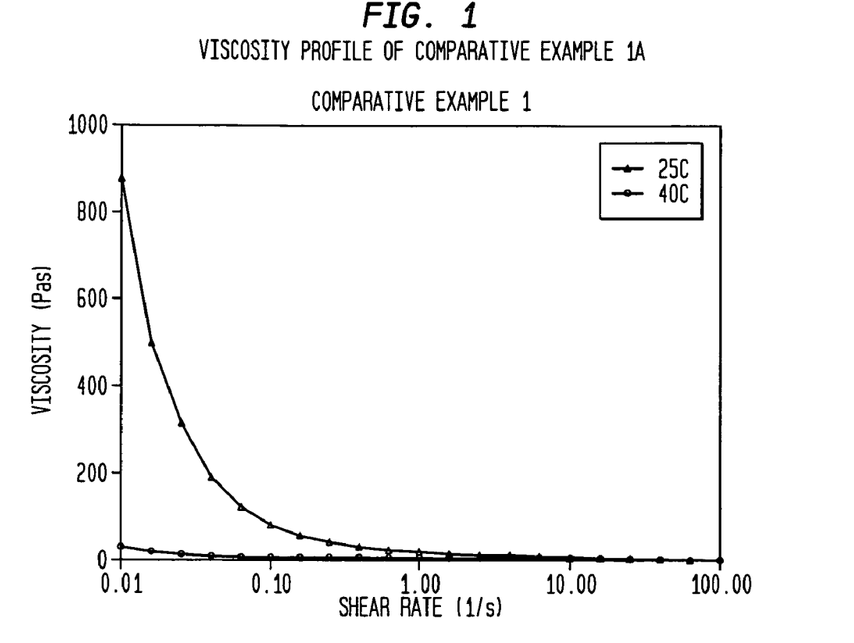
FIG. 1 is temperature effect on the viscosity profile of liquid composition containing only fatty acyl isethionate surfactant product without the specific elevated temperature stabilizer of this invention (Comparative example 1A of Table 3). The figure shows that the sample has a viscosity very sensitive to the storage temperature. At 25° C., it has 875 Pas viscosity at 0.01 s$^{-1}$ with lotion-like consistency. At 40° C., it became a water-thin liquid with a viscosity of only 20.5 Pas at 0.01 s$^{-1}$. The viscosity ratio of 40° C., to 25° C., is 0.0234 at the shear rate of 0.01 s$^{-1}$; and the sample showed phase separation at 45° C., storage condition in less than 1 week.
Figure 2:
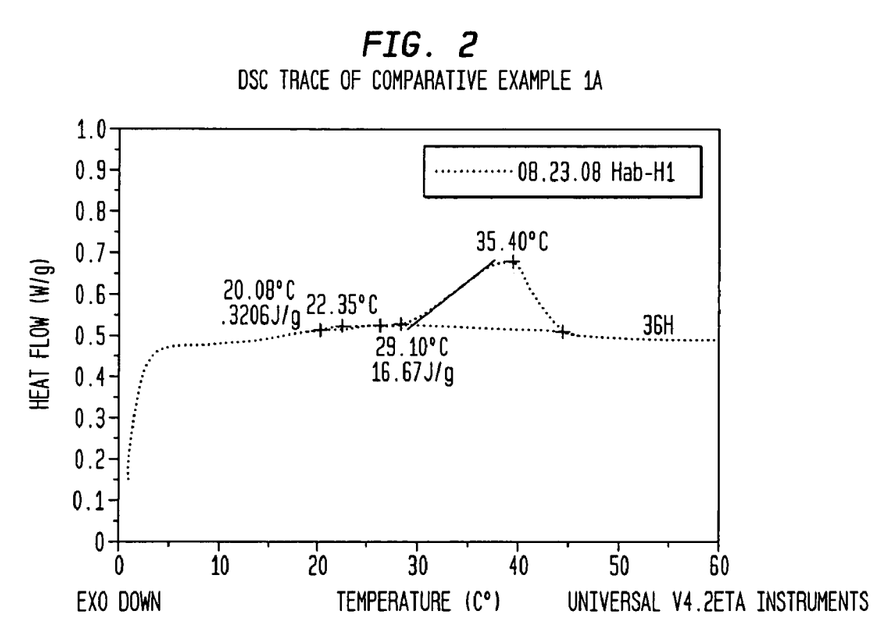
FIG. 2 is DSC thermogram of Comparative example 1A.

Depending on the processing conditions used, the resulting fatty acyl isethionate product can be a mixture of 45 to 95% by weight of fatty acyl isethionates and 50 to about 0 wt %, typically 40 to 5 wt % of free fatty acids, in addition to isethionates salts which are present typically at less than 5 wt %, and traces (less than 2 wt. %) of other impurities. Generally a mixture of aliphatic fatty acids is used for the preparation of commercial fatty acyl isethionates surfactants and resulting fatty acyl isethionate surfactants (e.g., resulting from reaction of alkali metal isethionate and aliphatic fatty acid) have at least 20 wt % (on basis of fatty acyl isethionates reaction product) of fatty acyl group with 14 or more carbon atoms and at least 16 wt % of fatty acids with 14 or greater carbon atoms. These longer chain fatty acyl isethionate surfactants and fatty acids form insoluble surfactant crystals typically in water at ambient temperatures. The fatty acyl isethionate/fatty acid crystals typically have a dissolution temperature between 30° and 45° C., as shown in FIG. 2 by measuring the crystal transition temperature of an aqueous solution containing only fatty acyl isethionate surfactant product in the liquid with a pH in the range of 6.0 to 7.5 (Comparative example 1A of Table 3) using differential scanning calorimetry (DSC) method described below. Due to the presence of these fatty acyl isethionate/fatty acid crystals, liquids containing these commercial fatty acid isethionate products in the liquid composition have very high viscosity at or below room temperature. At or above 40° C., however, the liquid turns into water thin liquid due to the dissolution of these surfactant crystals as shown in FIG. 1. This causes product inconsistency and storage instability at elevated temperatures (40° C. or above).

A key aspect of the present invention is that the extreme inconsistency of the fatty acyl isethionate product-containing liquid cleanser and its instability at elevated storage temperatures (40° C. or above) due to the dissolution of insoluble fatty isethionate/fatty acid crystals can be resolved using a specific fatty acids/fatty soap combination of this invention (i.e. elevated temperature stabilizing system described below) such that the resulting liquid composition can maintain its consistency and its stability by forming viscous surfactant liquid crystals at elevated storage temperatures (40° C. or above).

Particularly preferred fatty acyl isethionate products with 5 wt. % or more fatty acid/fatty soap which may now be consistently used include DEFI (Direct Esterification of Fatty Isethionate) flakes and synthetic detergent noodles produced from DEFI for personal cleanser application. DEFI flakes typically contain about 65 to 80 wt % of sodium fatty acyl isethionate and 15 to 30 wt % free fatty acids. More than 65 wt % of fatty acyl group of the resulting fatty acyl isethionates have 12 to 18 carbon atoms. Dove® cleansing bar noodles are mixtures of DEFI flakes described above and long chain (mainly C16 and C18) fatty acids and fatty soaps which contain about 40 to 60 wt % of fatty acyl isethionates and 30 to 40 wt % of fatty acids and fatty soaps. Examples of other commercial fatty acyl isethionate products that may be used in the invention are Hostapon® surfactants from Clariant such as Hostapon® SCI65C; Jordapon® CI, Jordapon® CI65; and sodium cocoyl isethionate from Yongan Daily Chemical Co. such as YA-SCI-75® or YA-SCI-65®. DEFI flakes and Dove® cleansing bar noodles produced by Unilever are particularly preferred for this application.

Synthetic Co-Surfactants

A second component of the subject invention are surfactants selected from the groups consisting of anionic surfactants, nonionic surfactants, zwitterionic surfactants, amphoteric surfactants as described below. The amount of synthetic co-surfactant used in the present invention can be in the range of 0 to 15 wt %. When determining level of co-surfactant, the amount of acyl isethionate surfactant formed is part of the acyl isethionate product is not counted.

The anionic surfactant may be, for example, an aliphatic sulfonate, such as a primary alkane (e.g., C$_8$-C$_{22}$) sulfonate, primary alkane (e.g., C$_8$-C$_{22}$) disulfonate, C$_8$-C$_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

wherein R is an alkyl or alkenyl having 8 to 18 carbons, preferably 12 to 18 carbons, n has an average value of greater than at least 0.5, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, alkyl and acyl glycinates, alkyl sulfoacetates, $C_8$-$C_{22}$ alkyl phosphates, alkyl phosphate esters and alkoxyl alkyl phosphate esters, acyl lactates, $C_8$-$C_{22}$ monoalkyl succinates and maleates, and branched acyl isethionates.

Another class of anionics are carboxylates such as follows:

wherein R is $C_8$ to $C_{20}$ alkyl; n is 1 to 20; and M is as defined above.

Another carboxylate which can be used is amido alkyl polypeptide carboxylates such as, for example, Monteine LCQ® by Seppic.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is $-CO_2-$ or $-SO_3-$

Amphoacetates and diamphoacetates are also intended to be covered in possible zwitterionic and/or amphoteric compounds which may be used.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Other surfactants which may be used are described in U.S. Pat. No. 3,723,325 to Parran Jr. and "Surface Active Agents and Detergents" (Vol. I & II) by Schwartz, Perry & Berch, both of which is also incorporated into the subject application by reference.

One preferred composition of the invention comprises acyl isethionate product with mixture of anionic (e.g., alkoxylated sulfate such as alkali metal alkyl ether sulfate) and amphoteric (e.g., betaine). In other embodiments, the isethionate product may be used with alkyl ether sulfate alone (see Example 7); with amphoteric alone (see Examples 4-6); or with no co-surfactant at all (see Examples 1 and 2).

Elevated Temperature Storage Stabilizing System

Another essential ingredient of the present invention is the elevated temperature storage stabilizing system which system comprises the combination of long chain and short chain linear fatty acids/fatty soaps. It was found that this specific combination defining the "elevated temperature storage stabilizing system" increases the viscosity of the liquid composition at or above 40° C., such that the viscosity of the liquid composition remains viscous enough to maintain its physical stability when stored at or above 40° C. While not wishing to be bound by theory, is believed that the specific combination defining elevated temperature storage stabilizing system changes the packing of the surfactant mixture of the liquid composition of this invention upon the dissolution of insoluble fatty acyl isethionate/fatty acid crystals at a temperature above its dissolution temperature to form viscous surfactant liquid crystal instead of low viscosity surfactant micelles such that the liquid maintains a high viscosity and maintains its physical stability. Long chain fatty acids in this invention are defined as linear fatty acids/fatty soaps with 16 to 20 carbons; and short chain fatty acids are linear fatty acids/fatty soaps with 14 or less carbon.

There are three criteria for the selection of fatty acids/fatty soaps mixture as elevated temperature storage stabilizing system of this invention. First, the total level of linear fatty acids/fatty soaps in the cleansing composition of this invention should be at least 4% up to 20% by weight of the composition. This includes the fatty acid/fatty soaps in the fatty acyl isethionate surfactant products added into the liquid cleansing composition in addition to what is separately in the composition. The second criteria is the ratio of total amount of the fatty acids/fatty soaps mixture to total amount of fatty acyl isethionate surfactant and co-surfactants in the cleansing composition is at least 0.25, preferably 0.30 and no more than 1.0. This is to ensure there is sufficient fatty acid/soap level required to stabilize the liquid. The last criteria is that amount of long chain fatty acids/fatty soaps ($>C_{14}$) should be no more than 70 wt % and at least 20 wt % of the total linear fatty acids/fatty soaps added to the liquid composition. Both the level and the composition of the fatty acids/fatty soaps required in the liquid composition of this invention can be determined by measuring the viscosity of the liquid cleanser composition of this invention containing various amount of long chain and short chain fatty acids/fatty soaps selected based on the three criteria described above using the viscosity method described below at both 25° C., and 40° C. The viscosity at 0.01 $s^{-1}$ should be at least 50 Pas, preferably 100 Pas at 25° C.; and the ratio of the viscosity at 40° C. to the viscosity at 25° C., at 0.01 $s^{-1}$ should be at least 0.2, preferably 0.3, most preferably 0.4. Other than the viscosity criteria described above, the liquid composition containing the desired combination of the liquid crystal modifiers should be stable at 45° C. for over 2 weeks.

Water Soluble/Dispersible Polymers

Water soluble/dispersible polymers are an optional ingredient that is preferred to be included in the liquid composition of the invention. The water soluble/or dispersible polymer can be cationic, anionic, amphoteric or nonionic polymer with molecular weight higher than 100,000 Dalton. These polymers are known to enhance in-use and after-use skin sensory feels, to enhance lather creaminess and lather stability, and to increase the viscosity of liquid cleanser compositions.

Examples of water soluble/or dispersible polymers useful in the present invention include the carbohydrate gums such as cellulose gum, microcrystalline cellulose, cellulose gel, hydroxyethyl cellulose, hydroxypropyl cellulose, sodium carboxymethylcellulose, hydroxymethyl or carboxymethyl cellulose, methyl cellulose, ethyl cellulose, guar gum, gum karaya, gum tragacanth, gum arabic, gum acacia, gum agar, xanthan gum and mixtures thereof; modified and nonmodified starch granules with gelatinization temperature between 30 to 85° C. and pregelatinized cold water soluble starch; polyacrylate; Carbopols; alkaline soluble emulsion polymer such as Aculyn 28, Aculyn 22 or Carbopol Aqua SF1; cationic polymer such as modified polysaccharides including cationic guar available from Rhone Poulenc under the trade name Jaguar C13S, Jaguar C14S, Jaguar C17, or Jaguar C16; cationic modified cellulose such as UCARE Polymer JR 30 or JR 40 from Amerchol; N-Hance 3000, N-Hance 3196, N-Hance GPX 215 or N-Hance GPX 196 from Hercules; synthetic cationic polymer such as MerQuat 100, MerQuat 280, Merquat 281 and Merquat 550 by Nalco; cationic starches, e.g., StaLok® 100, 200, 300 and 400 made by Staley Inc.; cationic galactomannans based on guar gum of Galactasol 800 series by Henkel, Inc.; Quadrosoft Um-200; and Polyquaternium-24.

Gel forming polymers such as modified or non-modified starch granules, xanthan gum, Carbopol, alkaline-soluble emulsion polymers and cationic guar gum such as Jaguar C13S, and cationic modified cellulose such as UCARE Polymer JR 30 or JR 40 are particularly preferred for this invention.

Water Soluble Skin Benefit Agents

Water-soluble skin benefit agents another optional ingredient that is preferred to be included in the liquid compositions of the invention. A variety of water-soluble skin benefit agents can be used and the level can be from 0 to 50 weight %, preferably 1 to 30%. The materials include, but are not limited to, polyhydroxy alcohols such as glycerin, propylene glycol, dipropylene glycol, sorbitol, pantenol and sugar; urea, alpha-hydroxy acid and its salt such as glycolic or lactic acid; and low molecular weight polyethylene glycols with molecular weight less than 20,000. Preferred water soluble skin benefit agents for use in the liquid composition are glycerin, sorbitol and propylene glycol.

The liquid cleansing composition of the invention also may comprise 0 to 40% by wt. benefit agent.

One class of ingredients are nutrients used to moisturize and strengthen, for example, the skin. These include:

a) vitamins such as vitamin A and E, and vitamin alkyl esters such as vitamin C alkyl esters;

b) lipids such as cholesterol, cholesterol esters, lanolin, creaminess, sucrose esters, and pseudo-ceramides;

c) liposome forming materials such as phospholipids, and suitable amphophilic molecules having two long hydrocarbon chains;

d) essential fatty acids, poly unsaturated fatty acids, and sources of these materials;

e) triglycerides of unsaturated fatty acids such as sunflower oil, primrose oil avocado oil, almond oil;

f) vegetable butters formed from mixtures of saturated and unsaturated fatty acids such as Shea butter;

g) minerals such as sources of zinc, magnesium, and iron;

A second type of skin benefit agent is a skin conditioner used to provide a moisturized feel to the skin. Suitable skin conditioners include:

a) silicone oils, gums and modifications thereof such as linear and cyclic polydimethylsiloxanes, amino, alkyl, and alkyl aryl silicone oils;

b) hydrocarbons such as liquid paraffins, petrolatum, Vaseline, microcrystalline wax, ceresin, squalene, pristan, paraffin wax and mineral oil;

c) conditioning proteins such as milk proteins, silk proteins and glutens;

d) cationic polymers as conditioners which may be used include Quatrisoft LM-200 Polyquaternium-24, Merquat Plus 3330-Polyquaternium 30; and Jaguar® type conditioners;

e) humectants such as glycerol, sorbitol, and urea;

f) emollients such as esters of long chain fatty acids, such as isopropyl palmitate and cetyl lactate.

A third type of benefit agent is deep cleansing agents. These are defined here as ingredients that can either increase the sense of refreshment immediately after cleansing or can provide a sustained effect on skin problems that are associated with incomplete cleansing. Deep cleansing agents include:

a) antimicrobials such as 2-hydrozy-4,2',4'-trichlorodiphenylether (DP300) 2,6-dimethyl-4-hydroxychlorobenzene (PCMX), 3,4,4'-trichlorocarbanilide (TCC), 3-trifluoromethyl-4,4'-dichlorocarbanilide (TFC), benzoyl peroxide, zinc salts, tea tree oil, b) anti-acne agents such as salicylic acid, lactic acid, glycolic acid, and citric acid, and benzoyl peroxide (also an antimicrobial agent), c) oil control agents including sebum suppressants, modifiers such as silica, titanium dioxide, oil absorbers, such as micro sponges, d) astringents including tannins, zinc and aluminum salts, plant extracts such as from green tea and Witch-hazel (Hammailes), e) scrub and exfoliating particles, such as polyethylene spheres, agglomerated silica, sugar, ground pits, seeds, and husks such as from walnuts, peach, avocado, and oats, salts, f) cooling agents such as methanol and its various derivatives and lower alcohols, g) fruit and herbal extracts, h) skin calming agents such as aloe vera, i) essential oils such as mentah, jasmine, camphor, white cedar, bitter orange peel, rye, turpentine, cinnamon, bergamot, citrus unshiu, calamus, pine, lavender, bay, clove, hiba, eucalyptus, lemon, starflower, thyme, peppermint, rose, sage, menthol, cineole, sugenol, citral, citronelle, borneol, linalool, geranoil, evening primrose, camphor, tymol, spirantol, penene, limonene and terpenoid oils.

Other benefit agents that can be employed include antiaging compounds, sunscreens, and in lightening agents.

When the benefit agent is oil, especially low viscosity oil, it may be advantageous to pre-thicken it to enhance its delivery. In such cases, hydrophobic polymers of the type describe in U.S. Pat. No. 5,817,609 to He et al. may be employed, which is incorporated by reference into the subject application.

The final liquid cleanser composition of the present invention should have a viscosity more than 50, preferably greater than 100 Pas measured at 0.01 s$^{-1}$ determined by a Rheometric Scientific SR5 Rheolmeter at 25° C., and the ratio of the viscosity at 40° C. to the viscosity at 25° C. at 0.01 s$^{-1}$ should be at least 0.2, preferably 0.3, most preferably 0.4 following the methodology for viscosity determination described below; and pH between 4.0 to 8.0, preferably 4.5 to 7.5. At ambient temperature, the composition contains surfactant crystals with dissolution temperature between 30° C. to 50° C. The compositions should also be physically phase stable at room temperature and 45° C. for at least two 2 weeks.

Other Optional Components

In addition, the compositions of the invention may include 0 to 10% by wt. optional ingredients as follows:

Perfumes; sequestering agents, such as tetra sodium ethylenediaminetetraacetate (EDTA), EHDP or mixtures in an amount of 0.01 to 1%, preferably 0.01 to 0.05%; and coloring agents, opacifiers and pearlizers such as zinc striate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenyl ether (DP300); preservatives such as dimethyloldimethylhydantoin (Glydant XL 1000), parabens, sorbic acid etc.

Antioxidants such as, for example, butylated hydroxytoluene (BHT) may be used advantageously in amounts of about 0.01% or higher if appropriate.

Polyethylene glycols as conditioners which may be used include:

| Polyox | WSR-25 | PEG 14M, |
| Polyox | WSR-N-60K | PEG 45M, or |
| Polyox | WSR-N-750 | PEG 7M. |

Another ingredient which may be included are exfoliants such as polyoxyethylene beads, walnut shells and apricot seeds.

Examples & Protocol

Methodology of Differential Scanning Calorimetry (DSC)

Samples were weighed into an aluminum pan, hermetically sealed, and loaded into a 2920 MDSC machine from TA Instruments at 25° C. The sample was equilibrated to a temperature of 2° C., Iso-Track for 2 minutes followed by heating at 5° C./min to 60° C.

Methodology for Viscosity Measurement

Viscosity was measured using AR-G2 controlled-stress Rheometer from TA Instruments either with steady rate sweep test method or peak hold test method. Procedures and set up for each test method to measure the cleanser's viscosity are described below:

| Test method A: | Steady Rate Sweep Method |
| Geometry: | Cone and Plate |
| Diameter: | 40 mm |
| Cone Angle: | 2° |
| GAP: | 0.061 mm |

Experimental Conditions:

| Test Type: | Steady Rate Sweep |
|---|---|
| Shear Rate Ramp: | from 0.01 to 100 s$^{-1}$ (log mode, 5 points per decade) |
| Measurement Time: | 40 seconds |
| Temperature: | Various (25° C./40° C.) |

Procedure:

About 0.5 g of sample was poured on to the plate. Cone was lowered to the gap of 0.1 mm and excess of sample was removed using plastic spatula. Gap was reduced to 0.061 mm and test was started. Shear rate vs. viscosity were plotted.

| Test method B: | Peak hold method |
|---|---|
| Geometry: | Standard Aluminum parallel plate |
| Diameter: | 40 mm |
| GAP: | 1000 micrometer |
| Test settings: | hold shear rate (1/s) at 0.01 |
| Duration | 50 seconds |
| Sampling delay time | 10 seconds |
| Temperature: | various (25 c./40 c.) |

Procedure:

About 2 g of sample was poured on to the plate. Plate was lowered to the gap of 1000 micrometer and excess of sample was removed using plastic spatula. Test was started and 5 readings were obtained. 1$^{st}$ reading was omitted and averages of last 4 reading were used.

Examples of compositions of the invention are set forth below (all the numbers in the tables are wt % of each ingredient as 100% active in the liquid composition):

TABLE 1

Examples 1 to 7 of this invention

| | Example # | | | | | | |
|---|---|---|---|---|---|---|---|
| | 1 | 2 | 3 | 4 | 5 | 6 | 7 |
| Dove ® Bar Noodle (fatty acyl isethionate product) | 36 | 36 | 30 | 30 | 20 | 20 | 24 |
| Jordapon Cl ex. ICI (fatty acyl isethionate product) | 0 | 0 | 3 | 3 | 3 | 3 | — |
| Na lauryl sulfosuccinate (Makanate LO ex. McINTYRE Group) | 0 | 0 | 0 | 3 | 3 | 3 | — |
| Na Lauryl 1EO sulfate (Steol 170 ex. Stepan) | — | — | — | — | — | — | 12 |
| Jaguar C13S (cationic polymer) | — | — | — | — | — | — | 0.1 |
| Lauric acid (C$_{12}$ fatty acid) | 5 | 3 | 5 | 4 | 5 | — | 5 |
| Coco fatty acid | — | — | — | — | — | 8 | — |
| Glydant plus | 0.2 | 0.2 | 0.2 | 0.2 | 0.2 | 0.2 | 0.2 |
| EDTA | 0.02 | 0.02 | 0.02 | 0.02 | 0.02 | 0.02 | 0.02 |
| Perfume | 0.3 | 0.3 | 0.3 | 0.3 | 0.3 | 0.3 | 1.2 |
| Total linear fatty acid/fatty soap | 17.6 | 15.6 | 15.7 | 14.65 | 11.8 | 15.15 | 13.4 |
| Fatty acid/soap longer than 14 carbons | 9.99 | 9.99 | 8.34 | 8.34 | 5.57 | 7.01 | 6.65 |
| Wt % of fatty acid/fatty soap longer than 14 carbons in total linear fatty acid/soap | 56.7 | 64 | 53.1 | 56.7 | 45.8 | 46.2 | 49.5 |
| Total synthetic surfactants | 18 | 18 | 17.6 | 20.6 | 15.6 | 15.6 | 24 |
| Ratio of total linear fatty acid/fatty soap to total synthetic surfactants | 0.98 | 0.87 | 0.89 | 0.71 | 0.76 | 0.97 | 0.54 |
| Viscosity (Pas) at 25° C. at 0.01 s$^{-1}$ | 12533 | 8121 | 4845 | 5436 | 1880 | 967 | 2413 |
| Viscosity (Pas) at 40° C. at 0.01 s$^{-1}$ | 9247 | 3433 | 4524 | 2702 | 1118 | 1320 | 1642 |
| 40° C./25° C. viscosity ratio | 0.74 | 0.42 | 0.93 | 0.50 | 0.59 | 1.37 | 0.68 |

*Dove ® bar, as unfragranced noodles

TABLE 2

Examples 8 to 17 of this invention

| | Example # | | | | | | | | | |
|---|---|---|---|---|---|---|---|---|---|---|
| | 8 | 9 | 10 | 11 | 12 | 13 | 14 | 15 | 16 | 17 |
| Dove ® Bar Noodle (fatty acyl isethionate product) | 12 | 12 | 12 | — | 8 | 4 | 10 | 10 | 16 | 16 |
| DEFI (fatty acyl isethionate product) | — | — | — | 12 | — | — | — | — | — | — |
| Jordapon Cl ex. ICI (fatty acyl isethionate product) | — | — | — | — | 2 | — | | | | |
| Na Lauryl 1EO sulfate (Steol 170 ex. Stepan) | 5.9 | 5.9 | 5.5 | 5.9 | 5.9 | 3 | 6 | 6 | 6 | 6 |
| Na cocoamidopropyl betaine (Tergo betaine F ex. Goldschmidt) | 3 | 3 | 5.5 | 3 | 3 | 9 | 6 | 6 | 6 | 6 |
| Lauric acid | 1 | — | 3 | 3.5 | 3.0 | 4 | 4 | 2 | 5 | 2.5 |
| Capric acid | 2.5 | 2.5 | — | — | — | — | — | — | — | — |
| Isostearic acid | 0.5 | — | 0.5 | 0.5 | 0.5 | 0 | — | — | — | — |
| Jaguar C13S | 0.1 | 0.1 | 0.3 | 0.1 | 0.1 | 0.1 | 0.1 | 0.1 | 0.1 | 0.1 |
| Starch (PureGel B990 ex. Grain Processing) | — | — | — | — | 2 | — | — | — | — | — |
| Petrolatum (Penreco Snow ex. Penreco) | — | — | 20 | — | — | — | — | — | — | — |
| Glycerine | — | — | 5 | — | — | — | 3 | 3 | — | — |
| Glydant plus | 0.2 | 0.2 | 0.2 | 0.2 | 0.2 | 0.2 | 0.2 | 0.2 | 0.2 | 0.2 |
| EDTA | 0.02 | 0.02 | 0.02 | 0.02 | 0.02 | 0.02 | 0.02 | 0.02 | 0.02 | 0.02 |
| Perfume (Dove DMB) | 1.2 | 1.2 | 1.2 | 1.2 | 1.2 | | 1.2 | 1.2 | 1.2 | 1.2 |
| Total linear fatty acid/fatty soap | 8.2 | 6.7 | 7.7 | 6.64 | 6.4 | 5.4 | 7.5 | 5.5 | 10.6 | 8.1 |
| Fatty acid/soap longer than 14 carbons | 3.83 | 3.33 | 3.33 | 2.31 | 2.71 | 1.11 | 2.77 | 2.77 | 4.44 | 4.44 |
| Wt % of fatty acid/fatty soap longer than 14 carbons in total linear fatty acid/soap | 46.7 | 49.6 | 43.2 | 34.8 | 42.5 | 20.6 | 36.9% | 50.3 | 41.9 | 54.8 |
| Total synthetic surfactants | 14.9 | 14.9 | 17 | 17.5 | 14.6 | 14 | 17 | 17 | 20 | 20 |
| Ratio of total linear fatty acid/fatty soap to total synthetic surfactants | 0.55 | 0.45 | 0.45 | 0.38 | 0.44 | 0.39 | 0.44 | 0.32 | 0.53 | 0.41 |
| Viscosity (Pas) at 25° C. at 0.01 s$^{-1}$ | 2472 | 1486 | 6123 | 1141 | 649 | 777 | 1114 | 109 | 3438 | 193 |
| Viscosity (Pas) at 40° C. at 0.01 s$^{-1}$ | 1954 | 1319 | 5270 | 795 | 926 | 1079 | 1405 | 91 | 4038 | 449 |
| 40° C./25° C. viscosity ratio | 0.79 | 0.89 | 0.86 | 0.70 | 1.43 | 1.39 | 1.26 | 0.83 | 7.63 | 2.32 |

*Dove ® bar, as unfragranced noodles

All examples in Table 1 and Table 2 were prepared by mixing all the ingredients except perfume, glydant plus and EDTA at 70 to 75° C. for 30 to 50 minutes until all the solid ingredients such as Dove® noodle, DEFI flake, Jordapon Cl and fatty acids dissolved to form an uniform mixture. Perfume, glydant plus (a hydantoin preservative) and ammonium sulfate were added after the liquid was cooled below 40° C. The pH of these liquids was adjusted to 5.5 to 7.0 using either 30% citric acid or 25% NaOH solution. Both DEFI and Dove® are fatty acyl isethionate products manufactured by Unilever. DEFI has about 72.5 wt % of C8 to C18 fatty acyl isethionates and 22 wt % free fatty acids of 8 to 18 carbons. Dove® is prepared by mixing about 65-75 wt % of DEFI with 15-25 wt % of long chain (C16 to C18) fatty acid and fatty soap. Dove® noodle contains about 50 wt % of fatty acyl isethionate surfactant, and about 35 wt % of linear fatty acid/linear fatty soap in which about 79.2 wt % of the fatty acid/fatty soap have more than 14 carbons. Jordopon CI is available from ICI. It has about 86 wt % of cocoyl fatty isethionate and 5 wt % of free coco fatty acids.

Samples were stored at room temperature and 45° C. for over 4 weeks. The viscosity data measured at both 25 and 40° C. are shown in the table. At 25° C., all the samples of this invention as shown in Tables 1 and 2 have a viscosity more than 100 Pas at 0.01 s$^{-1}$ and a viscosity ratio of 40° C. to 25° C. measured at 0.01 s$^{-1}$ higher than 0.4. They were stable at both 25 and 45° C. after storage for over 4 weeks, without visible physical separation. These examples indicate that the defined stabilization system of the invention is sufficiently robust to stabilize fatty acyl isethionate surfactant products containing high level of fatty acid/fatty soap (i.e., when used with the elevated temperature storage stabilizing system, compositions are consistently stable at both high and low temperature for at least 4 weeks regardless of fatty acid content and/or chain length of fatty acyl group).

TABLE 3

Comparative examples

| | Example # | | | | | |
|---|---|---|---|---|---|---|
| | 1A | 5A | 11A | 12A | 14A | 16A |
| Dove ® Bar Noodle (fatty acyl isethionate product) | 36 | 20 | 12 | 8 | 10 | 16 |

TABLE 3-continued

Comparative examples

| | Example # | | | | | |
|---|---|---|---|---|---|---|
| | 1A | 5A | 11A | 12A | 14A | 16A |
| Jordapon Cl ex. ICI (fatty acyl isethionate product) | — | 3 | — | 2 | — | — |
| Na lauryl sulfosuccinate (Makanate LO ex. McINTYRE Group) | — | 3 | — | — | — | — |
| Na Lauryl 1EO sulfate (Steol 170 ex. Stepan) | — | — | 5.9 | 5.9 | 6 | 6 |
| Na cocoamidopropyl betaine (Tergo betaine F ex. Goldschmidt) | — | — | 3 | 3 | 6 | 6 |
| Glycerin | — | — | — | — | 3 | — |
| ASAD (mixture of 51% palmitic/49% stearic acids) | — | 5 | — | — | — | — |
| Lauric acid | 0 | 0 | 0 | 0 | 0 | 0 |
| Jaguar C13S | — | — | 0.1 | 0.1 | 0.1 | 0.1 |
| Starch (PureGel B990 ex. Grain Processing) | — | — | — | 2 | — | — |
| Glydant plus | 0.2 | 0.2 | 0.2 | 0.2 | 0.2 | 0.2 |
| EDTA | 0.02 | 0.02 | 0.02 | 0.02 | 0.02 | 0.02 |
| Perfume | 0.3 | 0.3 | 1.2 | 1.2 | 1.2 | 1.2 |
| Total linear fatty acid/fatty soap | 12.24 | 12.15 | 4.2 | 2.9 | 3.5 | 5.6 |
| Fatty acid/soap longer than 14 carbons | 9.99 | 10.6 | 3.33 | 2.24 | 2.77 | 4.44 |
| Wt % of fatty acid/fatty soap longer than 14 carbons in total linear fatty acid/soap | 79.3 | 87.0 | 79.3 | 77.1 | 79.3 | 79.3 |
| Total synthetic surfactants | 18 | 15.6 | 14.9 | 14.6 | 17 | 20 |
| Ratio of total linear fatty acid/fatty soap to total synthetic surfactants | 0.68 | 0.76 | 0.28 | 0.20 | 0.21 | 0.28 |
| Viscosity (Pas) at 25° C. at 0.01 s$^{-1}$ | 875 | 908 | 11 | 21 | 15 | 27 |
| Viscosity (Pas) at 40° C. at 0.01 s$^{-1}$ | 20.5 | 51 | 4 | 5 | 16 | 25 |
| 40° C./25° C. viscosity ratio | 0.023 | 0.056 | 0.36 | 0.25 | 1.06 | 0.93 |

*Dove ® bar, as unfragranced noodles

Comparative examples, 1A, 5A, 11A, 12A, 14A and 16A as shown in Table 3 with compositions similar to Examples 1, 5, 11, 12, 14 and 16 of Tables 1 and 2 respectively, without the specific fatty acid mixture as claimed of this invention, i.e. no more than 70 wt % of the total fatty acids/fatty soaps in the liquid composition with more than 14 carbons, were prepared for comparison. All the comparative examples were prepared the same way described above. The composition of these comparative examples, except Comparative 1A, all are described in U.S. Pat. Nos. 5,132,037, 5,234,619 and 5,290,471 to Greene et al. None of these comparative samples were stable at 45° C. for over 2 weeks, and all showed phase separation in less than 2 weeks due to the lack of the right fatty acid mixture required to stabilize the liquid composition. Specifically, all the Comparative Examples (1A, 5A, 11A, 12A, 14A and 16A) had a fatty acid mixture with substantially high level of C16, C18 long chain fatty acids/fatty soaps as a ratio to total linear fatty acids/soaps (e.g., more than 75%) compared to what is disclosed in U.S. Pat. No. 5,132,037 by Greene et al. All the comparative examples either did not have high enough viscosity at 25° C., (comparative examples 11A, 12A 14A and 16A) or had a viscosity ratio at 25° C. to 40° C. less than 0.20 (Comparative Examples 1A and 5A).

FIG. 2 discloses a DSC trace of Example 1A which shows that, when required parameters of invention are not met, there is rapid drop in viscosity at about 40° C., (as indicated from drop in heat flow). This is also more directly shown in FIG. 1 previously discussed.

What is claimed is:

1. A personal liquid skin or hair cleansing composition comprising:
   (a) 3 to 45 wt % of fatty acyl isethionate surfactant product wherein said product comprises fatty acyl isethionate as well as free fatty acids and/or fatty soaps in the said product;
   (b) 0 to 15% wt % of a co-surfactant selected from the group consisting of anionic, amphoteric and nonionic surfactants and mixture thereof, wherein said co-surfactant excludes fatty acyl isethionate present in the product of (a);
   (c) 4 to 20 wt % C8 to C20 total linear fatty acids/fatty soaps in which fatty acids/fatty soaps with carbon chain length longer than 14 comprise 20 to 70 wt % by wt. of said total linear fatty acids/fatty soaps in the composition, wherein said total linear fatty acids/fatty soaps comprise both the free fatty acids/fatty soaps in the fatty acyl isethionate surfactant product of (a) as well as those found in the composition;
   wherein the ratio of total linear fatty acid/fatty soap to total synthetic surfactants is at least 0.25 and less than 1.0, wherein said total synthetic surfactants are defined as the sum of fatty acyl isethionate surfactant of item (a) and synthetic cosurfactant of item (b);
   wherein viscosity of the said liquid cleanser composition measured at 0.01 s$^{-1}$ and temperature of 25° C. is at least 50 Pas; and the ratio of the viscosity at 40° C. to the viscosity at 25° C., when measured at 0.01 s$^{-1}$, is at least 0.2;

wherein the pH of the liquid composition is in the range of 4.0 to 8.0;

wherein said composition is physically stable and will not partition as can be visually observed at 45° C. for at least 2 weeks.

2. A composition according to claim 1, wherein the fatty acyl isethionate surfactant product contains more than 10 wt % of free fatty acids/fatty soaps.

3. A composition according to claim 1, wherein the fatty acyl isethionate surfactant product contains more than 15 wt % of free fatty acids/fatty soaps.

4. A composition according to claim 1, wherein viscosity is at least 100 Pas.

5. A composition according to claim 1, wherein ratio of viscosity at 40° C. to 25° C. is at least 0.3.

6. A composition according to claim 1, comprising 8 to 35% fatty acyl isethionate product.

* * * * *